United States Patent
Wright et al.

(10) Patent No.: US 9,535,042 B2
(45) Date of Patent: Jan. 3, 2017

(54) METHOD AND SYSTEM FOR MONITORING BIOMOLECULE SEPARATIONS BY MASS SPECTROMETRY

(71) Applicant: Microsaic Systems Plc, Woking, Surrey (GB)

(72) Inventors: Steven Wright, Woking (GB); Alexander Iain McIntosh, Woking (GB)

(73) Assignee: MICROSAIC SYSTEMS PLC, Woking, Surrey (GB)

( * ) Notice: Subject to any disclaimer, the term of this patent is extended or adjusted under 35 U.S.C. 154(b) by 0 days.

(21) Appl. No.: 14/789,037

(22) Filed: Jul. 1, 2015

(65) Prior Publication Data
US 2016/0003787 A1 Jan. 7, 2016

(30) Foreign Application Priority Data

Jul. 2, 2014 (GB) .................. 1411840.0

(51) Int. Cl.
*G01N 30/72* (2006.01)
*G01N 33/487* (2006.01)
(Continued)

(52) U.S. Cl.
CPC ...... *G01N 30/7233* (2013.01); *G01N 30/7266* (2013.01); *G01N 33/487* (2013.01);
(Continued)

(58) Field of Classification Search
CPC .. H01J 49/0031; H01J 49/0431; H01J 49/165; H01J 49/04; G01N 2001/4016; G01N 2030/8813; G01N 2030/8881; G01N 30/6095; G01N 30/7233; G01N 30/7266; G01N 30/82; G01N 33/487; G01N 2030/009

See application file for complete search history.

(56) References Cited

U.S. PATENT DOCUMENTS

| | | | |
|---|---|---|---|
| 6,318,157 B1* | 11/2001 | Corso | G01N 30/466 210/198.2 |
| 2001/0038071 A1* | 11/2001 | Nichols | H01J 49/04 250/288 |

(Continued)

FOREIGN PATENT DOCUMENTS

| | | |
|---|---|---|
| EP | 1300679 | 4/2003 |
| WO | 20080024500 | 2/2008 |

OTHER PUBLICATIONS

Canarelli, S., et al., "On-line microdialysis of proteins with high-salt buffers for direct coupling of electrospray ionization mass spectrometry and liquid chromatography", Journal of Chromatography, vol. 948, No. 1-2, Mar. 2002, pp. 139-149.*

(Continued)

*Primary Examiner* — Wyatt Stoffa
(74) *Attorney, Agent, or Firm* — Stephen T. Scherrer; Monique A. Morneault; Scherrer Patent & Trademark Law, P.C.

(57) ABSTRACT

Monitoring biomolecule separations by mass spectrometry is described. The mixture to be separated is introduced into a first fluidic stream, which then passes through a chromatography column. Small samples are periodically taken from the first fluidic stream as it leaves the chromatography column and injected into a first branch of a second fluidic stream. Low molecular weight components detrimental to the efficient operation of the mass spectrometer are removed by an in-line dialysis cell. A second fraction of the second fluidic stream acts as the dialysate. In a second and preferred system provided in accordance with the present teaching, the first fraction of the second fluidic stream is further split downstream of the sampling mechanism through the use of a three-way connector. Approximately 0.3 to 5 microliters (Continued)

per minute continues through the dialysis cell and thereafter to the electrospray emitter of the mass spectrometer.

25 Claims, 12 Drawing Sheets

(51) Int. Cl.
G01N 30/82 (2006.01)
H01J 49/16 (2006.01)
G01N 1/40 (2006.01)
G01N 30/88 (2006.01)
G01N 30/60 (2006.01)
H01J 49/00 (2006.01)
H01J 49/04 (2006.01)

(52) U.S. Cl.
CPC ......... G01N 30/6095 (2013.01); G01N 30/82 (2013.01); G01N 2001/4016 (2013.01); G01N 2030/8813 (2013.01); G01N 2030/8881 (2013.01); H01J 49/0031 (2013.01); H01J 49/0431 (2013.01); H01J 49/165 (2013.01)

(56) References Cited

U.S. PATENT DOCUMENTS

2003/0017077 A1* 1/2003 Hahn ..................... G01N 1/34
422/81
2004/0041091 A1* 3/2004 Bateman ............. H01J 49/0031
250/282
2005/0019774 A1* 1/2005 Horn ..................... B01D 61/28
435/6.11

OTHER PUBLICATIONS

Cai, H., et al., "A straightforward means of coupling preparative high-performance liquid chromatography and mass spectrometry", Rapid Communication is Mass Spectrometry, col. 16, No. 6, Mar. 2002, pp. 544-554.*
Canarelli, S., et al., "On-line microdialysis of proteins with high-salt buffers for direct coupling of electrospray ionization mass spectrometry and liquid chromatography" Journal of Chromatography, vol. 948, No. 1-2, Mar. 2002, pp. 139-149.*
Cai H et al., "A Straightforward means of coupling preparative high-performance liquid chromatography and mass spectrometry," Rapid Communications in Mass Spectrometry, John Wiley 7 Sons, GB, vol. 16, No. 6, Mar. 30, 2002, pp. 544-554.
Liu C et al., "Direct coupling of ionic high-performance liquid chromatography with electrospray ionization mass spectrometry utilizing a microdialysis junction interface," Journal of Chromatography, Elsevier Science Publishers, B.V. NL, vol. 835, No. 1-2, Mar. 12, 1999, pp. 93-104.
EPO search report.
GB search report.
Journal of Chromatography A, vol. 948, No. 1-2, 2002, Canarelli S. et al., "On-line microdialysis of proteins with high-salt buffers for direct coupling of electrospray ionization mass spectrometry and liquid chromotography," pp. 139-149.
Anal. Chem. 1996, vol. 68, Liu et al., "On-Line Microdialysis Sample Cleanup for Electrospray Ionization Mass Spectrometry of Nucleic Acid Samples," pp. 3295-3299.

* cited by examiner

METHOD AND SYSTEM FOR MONITORING BIOMOLECULE SEPARATIONS BY MASS SPECTROMETRY

This application claims priority to UK Application Serial No. 1411840.0 filed Jul. 2, 2014, which is incorporated herein by reference.

TECHNICAL FIELD

The present invention relates to the separation of biomolecules by liquid chromatography and their subsequent detection by mass spectrometry. The invention more particularly relates to a method and system for removing low molecular weight components from the fluidic stream that would otherwise be detrimental to the operation of the mass spectrometer. Such a method and system may employ a dialysis cell.

BACKGROUND

Liquid chromatography is a method of separating the components of a mixture. In chemical and biochemical processing, the technique is used to purify a desired product, which may be mixed with by-products, starting materials, and reagents as a result of some previous processing step. In the field of chemical analysis, liquid chromatography is widely employed as a means of identifying and quantifying the components in a sample.

Separation occurs as the mixture is swept by a mobile fluidic phase through a column containing an immobile substrate referred to as the stationary phase. The rate at which any one component passes through the column depends on the nature of the interactions with the stationary phase. In general, the basis of these interactions may be adsorption, chemical bonding, polarity, solubility, or molecular filtration. The transit through a column of a component that interacts strongly with the stationary phase is retarded compared with a component that interacts weakly. Consequently, the components of a mixture emerge from the column at different times, allowing them to be collected or analysed separately.

It is normal practice to pass the fluidic stream through an ultraviolet (UV) absorption cell when it emerges from the column. The fluid within the cell is illuminated with UV light from a lamp, and the absorbance is measured with a photometer. This method of detection is non-destructive, and all of the flow may be passed through the cell without the components of the mixture undergoing any transformation. However, while good detection sensitivity can be achieved using UV absorption, even multiple wavelength or dispersive instruments are rarely capable of determining the chemical identities of the components with any confidence.

Alternatively, a mass spectrometer can be used to detect and identify the separated components. As the technique is destructive, only a small fraction of the fluidic stream should be diverted to the mass spectrometer if the intention is to make further use of the separated components. Those of skill in the art are aware that the molecular weight of a component can be deduced from its mass spectrum, and that this is often sufficient to identify the component with a high level of confidence.

Analysis by mass spectrometer requires that the biomolecules gain an electric charge and are released from solution. The resulting ions may then be separated according to their mass-to-charge ratio (m/z) by electric fields, magnetic fields, or combinations thereof and subsequently detected by an ion detector. Mass analysers are operated in vacuum to ensure that the trajectories of the ions are dominated by the applied fields rather than by collisions with neutral gas molecules. However, widely used methods of soft ionisation (techniques that generate ions without also causing fragmentation) operate at atmospheric pressure. Electrospray ionisation, atmospheric pressure chemical ionisation, and atmospheric pressure photo-ionisation are common examples. When one of these ionisation techniques is used, ions and ambient neutral gas molecules are drawn into the vacuum system housing the mass analyser through a small aperture. This aperture can become contaminated or blocked if high concentrations of involatile solutes are also present in the fluidic stream. While only electrospray ionisation will be considered below, it will be understood that many of the benefits of systems provided in accordance with the present teaching are also applicable when other forms of atmospheric pressure ionisation are employed.

In electrospray ionisation, the fluidic stream is passed through a capillary tube with a sharp tip to which a high voltage is applied. A partial separation of the positively and negatively charged ions in solution occurs in response to the electric field. Ions with the same polarity as the applied voltage become concentrated in an extruded volume at the tip of the emitter known as a Taylor cone. Droplets with an excess charge (an imbalance between the numbers of positive and negative ions) are ejected from the Taylor cone when the applied electric field is sufficient to overcome the surface tension of the fluid. Wholly aqueous solutions do not spray well, as the surface tension of water is high. Typically, an organic solvent that is miscible with water, such as acetonitrile or methanol, is added to the solvent system to reduce the surface tension. The charge density of a free droplet increases as solvent evaporates and its diameter decreases. This continues until such time as the electrostatic repulsion between like charges exceeds the surface tension, and the droplet undergoes fission. The fissioning of successive generations of progeny droplets eventually leads to the excess charge being carried by single ions surrounded by weakly bound shells of neutral solvent molecules.

Mass spectral peak intensities generally increase linearly with analyte concentration up to $10^{-5}$ to $10^{-3}$ M. At higher concentrations, the response levels-off or saturates. This is a reflection of the fact that the number of free ions produced cannot exceed the available excess charge. The chemical composition of the fluidic stream (the chemical identities of the solutes and their concentrations) is of great importance. The mass spectral peak intensity of an analyte of interest will normally decrease when the concentration of other solute ions is increased, as these compete for the finite amount of excess charge available. This phenomenon is known as ion suppression.

Those of skill in the art are aware that it is important to consider the mechanisms by which ions may be generated in solution prior to the electrospray process. Ionic compounds such as salts yield solvated positive and negative ions on dissolution and often give a strong response. Covalent compounds typically become charged through the addition of an acidic or a basic modifier to the solution. If the analyte has a basic moiety such as an amine, the addition of an acid to the solvent system results in protonation and the generation of positively charged ions. Formic acid at a concentration of 0.1% (v/v) is often used. If the analyte has an acidic moiety such as a carboxylic acid group, the addition of a base results in deprotonation and the generation of negatively charged ions. Biomolecules typically have numerous basic or acidic centres and can consequently become multiply charged. Covalent compounds may also become charged by forming adducts. For example, if NaCl is present, proteins in solution can acquire a positive charge by forming adducts with the Na$^+$ ions. This somewhat complicates the interpretation of mass spectra as peaks due to protonation/deprotonation and adduct formation may be present, depending on the composition of the solution.

In view of the forgoing discussion, characteristics of electrospray ionisation mass spectrometry that are relevant to the analysis of components dissolved in a fluidic stream may be summarised as:

High concentrations of involatile solutes result in contamination of the vacuum interface.

The signal level associated with a component of interest can become suppressed by the presence of other solutes.

The response saturates when the overall concentration of solutes is in excess of $10^{-5}$ to $10^{-3}$ M.

Wholly aqueous solutions do not spray well as the surface tension is too high.

The ionisation of covalent compounds is promoted by acidic or basic modifiers.

It is therefore clear, and well understood by those of skill in the art, that while the information that can be derived from mass spectrometry is useful, its application in all fields is not trivial and indeed in certain instances, it may not be a suitable analysis tool at all.

In this context it is useful to appreciate that biomolecules require careful handling during chromatographic separations and other processing steps, as they are prone to chemical transformations and modifications that render them biologically inactive, a process known as denaturation. Proteins, peptides, polypeptides, antibodies, enzymes, hormones, oligosaccharides, lipids, nucleic acids, and oligonucleotides are examples of biomolecules. They can be derived from natural sources, or synthesised. While the molecular backbone of a biomolecule may remain intact unless subjected to harsh conditions, changes to the native secondary, tertiary, and quaternary conformations can result in a loss of bioactivity, reduced solubility, and a tendency to aggregate. Elevated temperatures, extremes of pH, organic solvents, and non-physiological concentrations of salt are known to cause denaturation. Consequently, biomolecules are typically stored and processed in solutions that mimic natural physiological environments, for example, tris-buffered saline (TBS), an aqueous solution of 50 mM tris(hydroxymethyl) aminomethane and 150 mM NaCl adjusted to pH 7.6 with hydrochloric acid. Higher NaCl concentrations are encountered during certain chromatographic techniques, including, for example, affinity chromatography.

Unfortunately, TBS and other similar buffers used in biochemical processing are incompatible with electrospray ionisation mass spectrometry. The high concentrations of buffering agent and NaCl result in strong ion suppression, complex mass spectra dominated by clusters and adducts, and contamination of the vacuum interface with involatile material. Furthermore, the solution is slightly alkaline, resulting in very limited protonation of basic centres. Any attempt to directly acidify the solution in order to promote protonation is initially counteracted by the buffering capacity of the buffer system. It will therefore be apparent that the analysis of biomolecules using mass spectrometry is not necessarily appropriate or feasible, as the carefully tailored aqueous buffers used to preserve the fragile native conformations of biomolecules result in low sensitivity, data analysis difficulties, and a need for frequent servicing of the vacuum interface.

It is known to address these problems using dialysis. Dialysis is a technique used in chemical processing to change the composition of solutions, and is ideally suited to the task of desalting biomolecule samples prior to analysis by mass spectrometry. It is an example of a mass transfer operation, a group of processes that can be employed to effect changes in composition without chemical reaction. In dialysis, two solutions with different compositions are separated by a semi-permeable membrane that allows the passage of molecules through narrow pores. In order to attain thermodynamic equilibrium, molecules diffuse from one side of the membrane to the other until the concentrations in the two solutions are equal. Usually, the aim is to substantially remove one or more unwanted low molecular weight components from a mixture while retaining desired high molecular weight components. This can be achieved if the pores in the membrane are wide enough to allow passage of the smaller molecules, but too narrow to transmit larger molecules.

Manual batch dialysis involves filling an envelope fabricated from semi-permeable membrane (often a section of tubing tied off at each end) with the solution to be dialysed. This is immersed in a bath containing a large volume of the second solution, or dialysate. Over the course of hours or even days, unwanted low molecular weight components diffuse out of the membrane envelope and into the dialysate, leaving behind a purified solution of the high molecular weight components. It is known to prepare biomolecule samples for mass spectrometric analysis using this method.

Flow processing by dialysis can be used for the in-line purification of fluidic streams, a familiar example being the clinical treatment of whole blood by haemodialysis machines. The technique involves pumping the fluidic stream to be purified through a first channel of a dialysis cell, and the dialysate through a second channel of the dialysis cell, the two channels being separated by a semi-permeable membrane. It is known to prepare biomolecule samples for mass spectrometric analysis using flow dialysis. Liu and co-workers have described in Analytical Chemistry vol. 68, 3295-3299 (1996) the clean-up and analysis of a very dilute solution of an oligonuleotide, which was pumped continuously through a flow dialysis cell and thereafter to an electrospray emitter by a syringe pump. The dialysate flow rate was at least sixty-fold greater than the flow rate of the oligonucleotide solution.

While this described process did achieve an analysis of biomolecules by mass spectrometry, there is a continued need for a means of repetitively sampling the effluent from a chromatography column, diluting the sampled material in a solvent system that aids the electrospray process, and efficiently performing dialysis on the resulting solution to remove components that would otherwise suppress the detection sensitivity, complicate the analysis, and contaminate the mass spectrometer. The process is required to be completed promptly so that the biomolecules emerging from the chromatography column can be identified without delay. Minimal dialysate consumption and a low-cost, compact, fluidic pumping arrangement are also desirable.

Liu and Verma have described an apparatus comprising a fluidic pump, a chromatography column, a needle valve splitter, a microdialysis assembly, and an electrospray ionisation mass spectrometer in the Journal of Chromatography A, vol. 835, 93-104 (1999). The needle valve splitter was set such that a minor fraction of the fluidic stream leaving the chromatography column was diverted to the dialysis assembly and thereafter the electrospray emitter. The dead volume of the dialysis assembly, including associated tubing was measured to be approximately 15-20 µL. Consequently, the flow rate through the dialysis system was chosen to be 10-20 µL/min so as to limit the delay to approximately 1 min, i.e. 1 min elapsed before material diverted from the main stream reached the electrospray emitter. A 2% solution of acetic acid in methanol was added to the flow at the electrospray emitter using a syringe pump in order to enhance the signal levels. Earlier introduction was avoided as the semi-permeable membrane used was intolerant of acidic conditions (pH<4), and because the authors believed that the efficiency of the dialysis process would be low in the presence of an organic solvent. The dialysate was separately supplied by gravity feed from a reservoir. Apart from the need for two additional fluidic streams (one to supply the dialysate and one to provide the acetic acid solution), a disadvantage of this configuration is that the flow rate through the dialysis cell is not independent of the flow rate through the chromatography column. If the latter is increased without also altering the needle valve setting, the residence time of the fluid in the dialysis cell decreases, leading to less efficient desalting. A further disadvantage of this configuration is that it is unsuitable for electrospray sources designed to operate at reduced flow. As the flow rate that may be accepted by the electrospray emitter also determines the flow rate through the entire dialysis assembly and associated tubing, the time taken for material diverted from the main stream to reach the electrospray emitter becomes unacceptably long when the operating regime is in the nanoliter to low microliter per minute range.

There therefore remain a number of problems associated with monitoring of biomolecule separations by mass spectrometry when the mobile phase is incompatible with common ionisation techniques and reliable operation of the vacuum interface.

SUMMARY

The present teachings provide a system and method that efficiently and conveniently facilitate monitoring of biomolecule separations by mass spectrometry when the mobile phase is incompatible with common ionization techniques and reliable operation of the vacuum interface.

The inventors have realized that the dependence of the flow rate through the dialysis cell on the flow rate through the chromatography column may be eliminated by employing a periodic sampling device to transfer discrete aliquots from the column effluent into a separately provided second fluidic stream. The flow rate through the dialysis cell, and hence, the efficiency of the dialysis process, is then entirely independent of the flow rate through the chromatography column. Furthermore, the inventors have recognized that the system may be simplified by using the fluidic stream originating from a single reservoir and pump to both flush the aliquots from the sampling device and act as the dialysate. Additionally, the inventors have understood that extension of the prior art to include electrospray emitters operating at low flow rates is advantageous in that less dialysate is consumed and the size of the dialysis cell may be reduced but necessarily results in long delays, since the rate of transit from the point of sampling to the emitter is dictated by the electrospray process. An embodiment of the invention described herein overcomes this problem by employing a high flow rate to convey the sample aliquots from the periodic sampling device to a downstream static fluidic split that then allows a small fraction of the flow to continue to a closely coupled dialysis cell and thereafter the spray emitter. Such an arrangement allows a quick response but also minimizes the amount of material to be dialyzed, and reduces the flow rate to a level consistent with low-flow electrospray.

An exemplary embodiment of a system provided in accordance with the present teaching comprises a means of periodically withdrawing a sample from the fluidic stream leaving the chromatography column, i.e. a sampling apparatus, a dialysis cell that removes unwanted low molecular weight components, and an electrospray emitter. The dialysis cell desirably has a sandwich structure in which two independent channels are separated by a semi-permeable membrane. In such an implementation, the system further comprises a second fluidic flow that is desirably split or bifurcated into two branches. The first branch is used to convey the samples from the sampling apparatus to a first channel of the dialysis cell and thereafter the electrospray emitter. The second branch is directed to the second channel of the dialysis cell where it acts as the dialysate.

Only a small amount of the fluidic stream leaving the chromatography column is withdrawn for dialysis and destructive analysis by mass spectrometry. Consequently, the majority of the potentially valuable separated biomolecule is retained in a buffer that preserves the secondary, tertiary, and quaternary structures. An advantage of a system provided in accordance with the present teaching is that only one additional fluidic pump is required to convey the sample from the sampling apparatus, dilute the samples to a concentration below the response saturation level of $10^{-5}$ to $10^{-3}$ M, mix the aqueous samples with an organic solvent and a chemical modifier to aid the electrospray process, and provide dialysate to the dialysis cell.

Another system provided in accordance with the present teaching may additionally comprise a static fluidic split between the sampling mechanism and the first channel of the dialysis cell. The fluidic split and the dialysis cell are intimately positioned in order to reduce the dead volume of the coupling between them. This arrangement allows the use of electrospray emitters designed for low flow operation while at the same time ensuring that the samples can be flushed quickly from the sampling mechanism.

In another embodiment in accordance with the present teaching, a system for effecting biomolecule separations and monitoring said separations by mass spectrometry is described, the system comprising: a liquid chromatography module configured to effect at least a partial separation of biomolecule components dissolved in a liquid, the dissolved biomolecule components being carried through the liquid chromatography module in a first fluidic stream; a sampling module in fluid communication with and provided downstream of the liquid chromatography module, the sampling module being configured to periodically transfer an aliquot of the liquid in the first fluidic stream into a second fluidic stream; a dialysis module in fluid communication with and provided downstream of the sampling module, the dialysis module being configured to dialyze the liquid in the second fluidic stream; and a mass spectrometer in fluid communication with and provided downstream of the dialysis module, the mass spectrometer being configured to detect components in the dialyzed liquid in the second fluidic stream; wherein operably, the first fluidic stream is provided at a first flow rate and the second fluidic stream is provided at a second flow rate, independent of the first flow rate.

The system wherein the dialysis module comprises a first channel and a second channel, the first channel being configured to receive the liquid to be dialyzed and the second channel being configured to receive a dialysate.

The system wherein the second fluidic stream comprises a first branch and a second branch, the first branch of the second fluidic stream operably receiving the transferred aliquot and thereafter passing through the first channel, the second branch of the second fluidic stream being operably directed through the second channel.

The system further comprising a flow splitting module configured to split the second fluidic stream, the flow splitting module being provided downstream of the sampling module and prior to the dialysis module, the splitting of the second fluidic stream effecting a reduction in the flow of liquid that is passed into the first channel and dialyzed by the dialysis module.

The system wherein the sampling module comprises a mass rate attenuator.

The system wherein the sampling module comprises a loop injection valve.

The system wherein the first and second channels of the dialysis module are separated by a semi-permeable membrane.

The system configured such that the flow rate of the second fluidic stream is in the range of 0.1 to 10 milliliters per minute.

The system comprising a reservoir in fluid communication with the second fluidic stream, the second fluidic stream operably being drawn from the reservoir by a pump.

The system comprising a syringe pump coupled to a syringe, wherein the second fluidic stream is operably expelled from the syringe by the syringe pump.

The system comprising a plurality of reservoirs of different composition in fluid communication with the second fluidic stream, the system further comprising a switching valve, an activation of the switching valve providing a selection of one reservoir from the plurality of reservoirs.

The system wherein the flow splitting module is co-fabricated with the first channel of the dialysis cell.

The system wherein the flow rate through the first channel of the dialysis cell is operably in the range of 0.2 to 5 microliters per minute.

The system wherein the first and second branches of the second fluidic stream flow through the dialysis module in opposite directions.

The system wherein the biomolecule components comprise at least one of proteins, peptides, polypeptides, antibodies, enzymes, hormones, oligosaccharides, lipids, nucleic acids, and oligonucleotides.

The system of wherein the first fluidic stream operably comprises one or more chemical species that are removed by dialysis prior to analysis of the transferred samples by mass spectrometry.

The system wherein chemical components selected from sodium chloride, potassium chloride, tris(hydroxymethyl)aminomethane, sodium phosphate, potassium phosphate, glycine, sodium acetate, sodium citrate, urea, ethylenediaminetetraacetic acid, and detergents are operably partially or fully removed from the second fluidic stream by dialysis.

The system wherein the first channel of the dialysis module is configured such that its volume is in the range of 0.10 to 2.5 µL.

The system wherein the first channel comprises at least one of supporting pillars, ribs, and beams, provided to prevent constriction of the first channel by the semi-permeable membrane.

The system wherein the dialysis module comprises polyether ether ketone, polytetrafluoroethylene, polyimide, polycarbonate, glass, ceramic, stainless steel, plastic, or silicon substrates.

The system wherein the semi-permeable membrane comprises cellulose ester, regenerated cellulose, or polyvinylidene fluoride.

The system wherein the chromatography module operably employs one or more of the techniques known as gel filtration, ultrafiltration, molecular filtration, ion exchange, size exclusion, hydrophobic interaction, or affinity chromatography.

The system wherein the second fluidic stream comprises one or more organic solvents selected from acetonitrile, methanol, isopropyl alcohol, and ethanol.

The system wherein the second fluidic stream comprises one or more chemical modifiers that aid the ionization process.

The system wherein the modifier is selected from formic acid, acetic acid, ammonium acetate, ammonium bicarbonate, glycerol, and m-nitrobenzyl alcohol.

The system wherein ionization is operably achieved by means of electrospray ionization, atmospheric pressure chemical ionization, atmospheric pressure photoionization, or derivatives thereof.

The system wherein a diverter valve is provided to divert the first fluidic stream into a collection vessel.

The system further comprising a logic module configured to vary the position of the diverter valve based on information derived from the mass spectrometer.

The system wherein a delay loop is fitted upstream of the diverter valve.

The system configured to store data from the mass spectrometer in the form of stored mass spectra, the system further configured to derive the molecular weights of detected components from the stored mass spectra.

The system configured to electronically tag or label collected portions of the first fluidic stream with mass spectra or molecular weights of biomolecules contained therein.

The system comprising at least one meter to monitor at least one of the fluidic streams passing through the first and second channels such that the efficiency of the dialysis process is indicated.

The system wherein the at least one meter comprises electrodes, the electrodes being integrated with the dialysis module.

The system configured to vary flow rates in the first or second channels according to the indicated efficiency.

The system wherein the dialysis module is heated.

The system wherein the dialysis module provides electrodialysis.

The system wherein multiple separations are monitored using a single mass spectrometer.

The system comprising a plurality of sampling modules and a plurality of chromatography modules, wherein each of the sampling modules may transfer aliquots from one of the chromatography modules into the second fluidic stream.

The system comprising an electrospray emitter.

The system provided in a modular construct, wherein at least the electrospray emitter and the dialysis module are provided as a demountable assembly.

The system, provided in a modular construct, wherein at least the electrospray emitter and the dialysis module are provided as a demountable assembly and wherein the first channel of the dialysis module and the electrospray emitter are provided as a monolithic structure.

The system wherein the molecular weight cut-off of the semi-permeable membrane is selected from the group comprising: (i) 3-10 kDa, (ii) 10-20 kDa, (iii) 20-40 kDa, (iv) 40-60 kDa, (v) 60-80 kDa, and (vi) 80-100 kDa.

In yet another embodiment in accordance with the present teaching, a system for effecting biomolecule separations and monitoring said separations by mass spectrometry is described, the system comprising: a liquid chromatography module configured to effect at least a partial separation of biomolecule components dissolved in a liquid, the dissolved biomolecule components being carried through the liquid chromatography module in a first fluidic stream; a sampling module in fluid communication with and provided downstream of the liquid chromatography module, the sampling module being configured to periodically transfer an aliquot of the liquid in the first fluidic stream into a second fluidic stream; a dialysis module in fluid communication with the sampling module, the dialysis module being configured to dialyze the liquid in the second fluidic stream, wherein the dialysis module comprises a first channel and a second channel, the first channel being configured to receive the liquid for dialyzing and the second channel being configured to receive a dialysate; a mass spectrometer in fluid communication with and provided downstream of the dialysis module, the mass spectrometer being configured to detect components in the dialyzed liquid in the second fluidic stream; and a flow splitting module for splitting the second fluidic stream, the flow splitting module being provided downstream of the sampling module and prior to the dialysis module, the splitting of the second fluidic stream effecting a reduction in the flow of liquid that is passed into the first channel and dialyzed by the dialysis module.

The system wherein the second fluidic stream comprises first and second branches, the first branch of the second fluidic stream operably receiving the transferred aliquot and thereafter passing through the first channel, the second branch of the second fluidic stream being operably directed through the second channel.

In yet another embodiment in accordance with the present teaching, a method of effecting biomolecule separations and monitoring said separations by mass spectrometry is described, the method comprising: using a liquid chromatography module to effect at least a partial separation of biomolecule components dissolved in a liquid, the dissolved biomolecule components being carried through the liquid chromatography module in a first fluidic stream; using a sampling module in fluid communication with and provided downstream of the liquid chromatography module, the sampling module being configured to periodically transfer an aliquot of the liquid in the first fluidic stream into a second fluidic stream; providing a dialysis module in fluid communication with and provided downstream of the sampling module, the dialysis module being configured to dialyze the liquid in the second fluidic stream; and providing a mass spectrometer in fluid communication with and provided downstream of the dialysis module, the mass spectrometer being configured to detect components in the dialyzed liquid in the second fluidic stream; wherein operably, the first fluidic stream is provided at a first flow rate and the second fluidic stream is provided at a second flow rate, independent of the first flow rate.

Accordingly the present teaching provides a system as defined in each of the independent claims. An independent method per the method claim is also provided. Advantageous features are provided in the dependent claims.

Additional features and advantages of the present invention are described in, and will be apparent from, the detailed description of the presently preferred embodiments and from the drawings.

BRIEF DESCRIPTION OF THE DRAWINGS

The present application will now be described with reference to the accompanying drawings in which.

Figure 1:
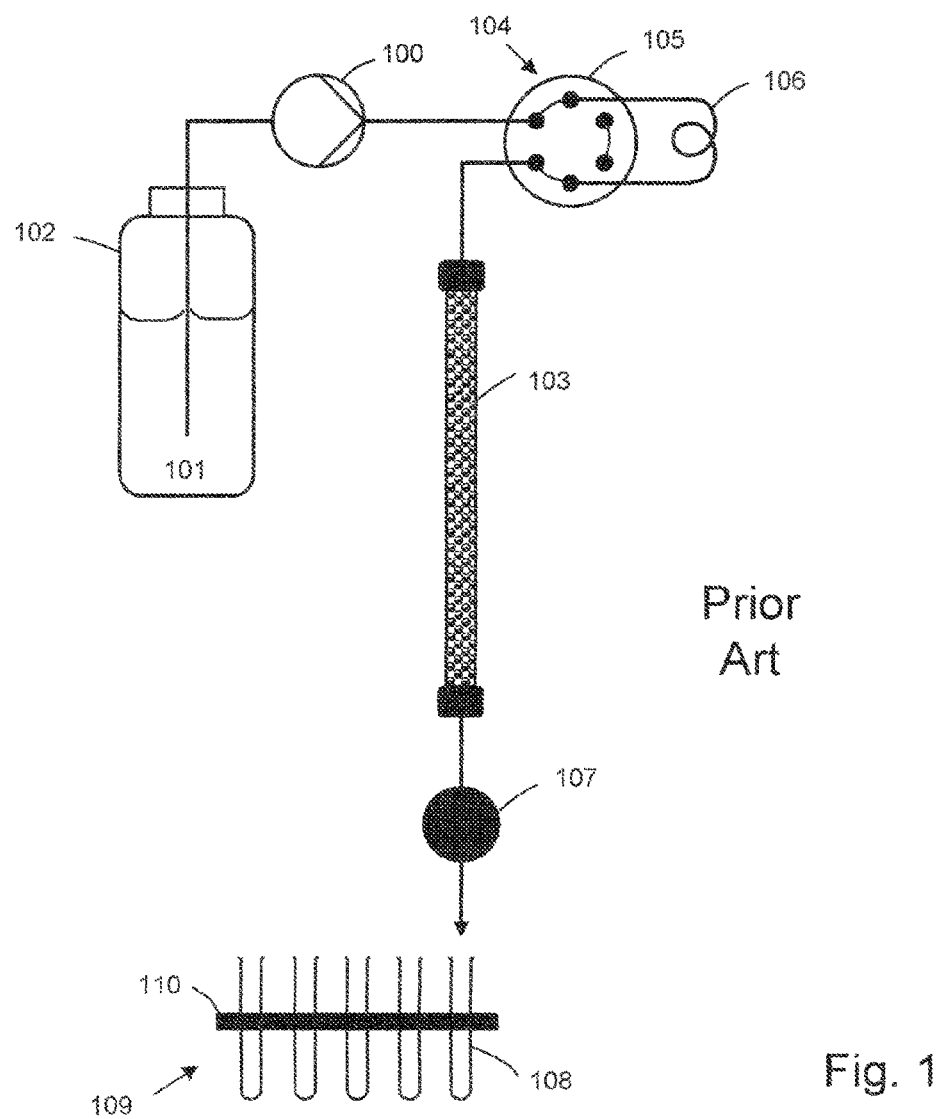
FIG. 1 shows a prior art column chromatography system equipped with a UV absorption detector.

The same reference numerals have been used throughout the drawings and following description to refer to the same or like components. Features of the drawings have not necessarily been drawn to scale. In the interests of clarity, not all of the routine features of the implementations described herein are shown or described.

DETAILED DESCRIPTION

FIG. 1 shows a typical separation system employing liquid chromatography. A pump 100 draws the mobile phase 101 from a reservoir 102 and supplies it to a column 103 at a set flow rate. The column may be considered a liquid chromatography module of the separation system. Liquid chromatography methods that can be applied to biomolecule separations include gel filtration, ultrafiltration, molecular filtration, ion exchange, size exclusion, hydrophobic interaction, and affinity chromatography. The optimum flow rate is determined by a number of considerations, including the composition of the mixture, the maximum tolerable pressure, the stationary phase particle size, the chemical selectivity of the stationary phase, and the dimensions of the column. Typical flow rates range from 0.1 to 10 milliliters per minute. In known alternative embodiments, a mobile phase of varying composition is provided by programmed mixing of fluidic streams drawn from two or more reservoirs.

A loop injection valve 104 comprising a switching mechanism 105 and a tubular loop 106 is used to introduce an aliquot of the mixture to be separated into the flowing mobile phase before it reaches the column 103. After leaving the chromatography column 103, the fluidic stream passes through a UV absorption cell 107. Separated components are detected as a series of peaks in a plot of the absorbance against time. Such a plot is referred to as a chromatogram, while the elapsed time between injection and the peak maximum is referred to as the retention time. The areas under the peaks can be used to quantitatively determine the amount of each component present.

The fluidic stream is collected in vials 108 by a fraction collector 109. As the separation proceeds, the rack 110 is periodically translated by an automatic mechanism as each vial is successively filled. The chromatogram is later inspected to determine which of the vials contains separated components of interest. Alternatively, a diverter valve may be used to collect the fluidic stream only when the presence of a component of interest is detected in the column effluent by the UV absorption cell. At other times the fluidic stream is passed to waste.

Figure 2:
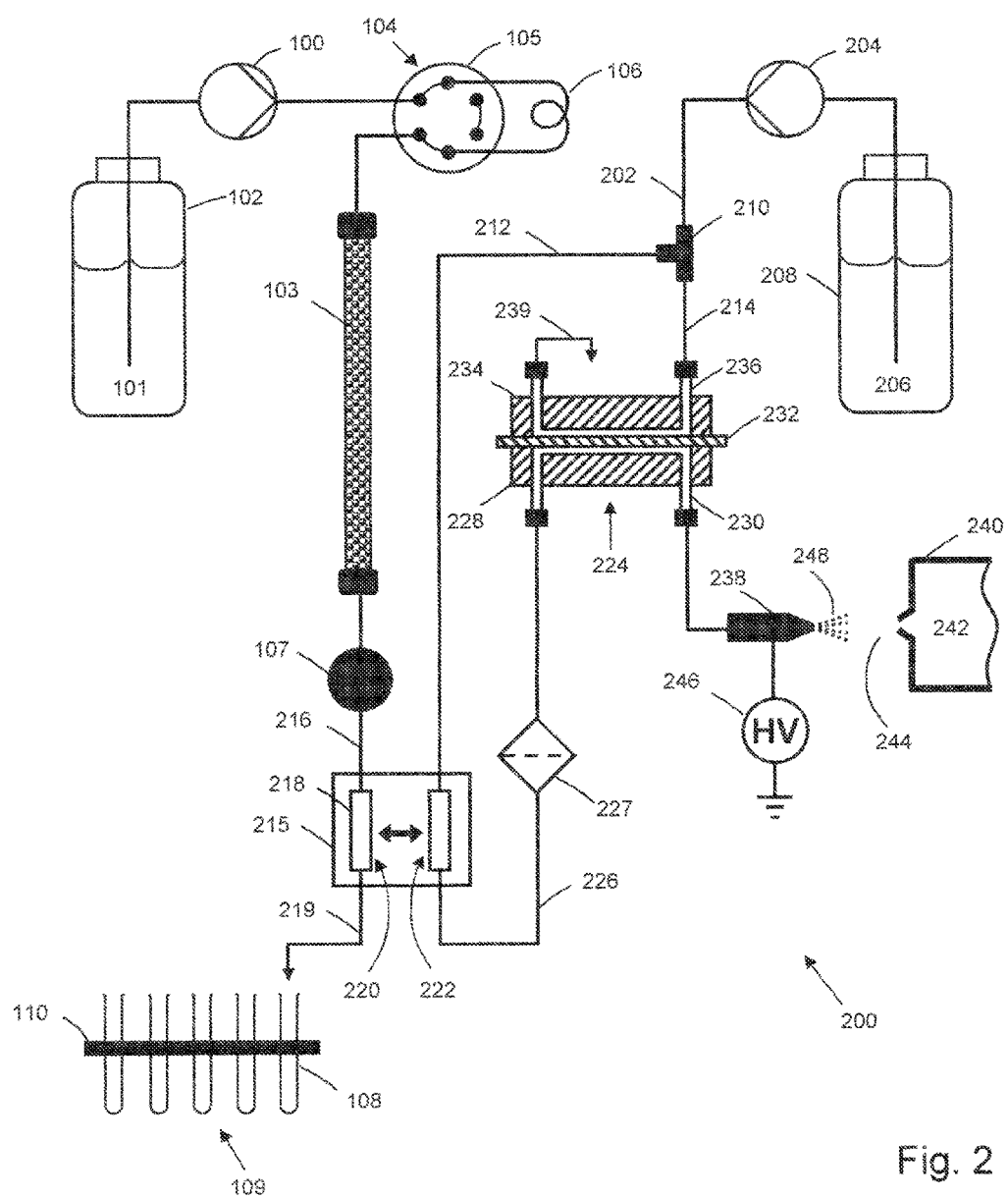
FIG. 2 shows a schematic representation of a system provided in accordance with the present teaching.

FIG. 2 shows a schematic representation of a first embodiment of a system provided in accordance with the present teaching. Components 100-110 fulfil the same functions as described in relation to FIG. 1. A second fluidic stream 202 is provided by a second pump 204 that draws a solvent system 206 from a reservoir 208, desirably at a rate of 0.1-10 mL/min. Both piston and peristaltic pumps are suitable for this purpose. Alternatively, the solvent may be expelled from a syringe by a syringe pump. The solvent system 206 advantageously comprises a mixture of water, an organic solvent, and a chemical modifier to promote protonation, deprotonation, adduct formation, or supercharging. Examples of suitable organic solvents are acetonitrile, methanol, isopropanol, and ethanol. Suitable chemical modifiers include formic acid, acetic acid, ammonium acetate, ammonium bicarbonate, glycerol, and m-nitrobenzyl alcohol. Greater flexibility is provided by a more complex configuration in which the second fluidic stream is drawn from one of several reservoirs, each filled with a different solvent system. The source of the second fluidic stream may be controlled using a multiple position valve, which is set, either before or during the chromatographic separation, according to the chromatographic method and/or the chemical characteristics of the biomolecules.

A bifurcation module, which may be provided in the form of a three-way connector 210, for example, causes the second fluidic stream 202 to split into a first branch 212 and a second branch 214. A sampling module in fluid communication with and provided downstream of the liquid chromatography module is configured to transfer an aliquot of the liquid from the first fluidic stream into the second fluidic stream. In this exemplary instance, the sampling module is provided in the form of a mass rate attenuator 215, such as the Rheodyne MRA manufactured by IDEX Corporation. It transfers an aliquot of the first fluidic stream 216 into the first branch of the second fluidic stream 212 at a position downstream of the chromatography column 103. A switching mechanism within the mass rate attenuator periodically translates a small chamber 218 from a first flow path 220 to a second flow path 222. The size of the chamber 218 and the frequency with which it is cycled between the two flow paths determines how much of the first fluidic stream is transferred into the first branch of the second fluidic stream. The optimum combination of switching frequency and chamber volume depends on the flow rate of the first fluidic stream, the amount of material on column, the value of the material on column, and the chromatographic peak widths. For the convenience of the user, the switching mechanism settings are desirably set automatically by a system computer according to the known chromatography method parameters.

The first branch of the second fluidic stream 212 conveys the samples from the mass rate attenuator 215 to a dialysis module or dialysis cell 224 through tubing 226. The dialysis cell is provided to effect dialysis of the liquid in the first branch of the second fluidic stream. Simultaneously, the initially discrete samples become mixed with and diluted by the solvent system 206 as a result of diffusion during transit of the tubing 226. If this process does not progress sufficiently, additional mixing may be induced by an in-line mixing device (not shown). It is possible that one or more components may precipitate during the mixing process. Accordingly, it is desirable to provide an in-line filter 227, preferably with a replaceable frit or screen, to trap particulates before they block the narrow channels of downstream components.

Multiple separations may be monitored using one mass spectrometer by means of a system of multiplexing. For example, the effluent from two chromatography columns may be sampled by two separate mass rate attenuators, the right-hand side flow paths 222 of which are linked in series such that samples from either column can be fed into the second fluidic stream. Only one mass rate attenuator can be active at any instant in order to avoid mixing of the samples from different columns.

The dialysis cell 224 is fabricated as a sandwich-like structure comprising a first block 228 carrying a first channel 230, a semi-permeable membrane 232, and a second block 234 carrying a second channel 236. Where they meet the inward-facing surfaces of the blocks, the two channels have open trench profiles, allowing the fluid passing through the channels to be in contact with the semi-permeable membrane. These trenches may be configured with straight or serpentine profiles. It is to be understood that an assembly comprising a jacketed semi-permeable capillary tube may alternatively be employed. In such a configuration, the solution to be dialyzed flows through the inner semi-permeable capillary, while the dialysate flows through the gap between the capillary and an outer, coaxial, tubular jacket.

Desirably, the inward-facing surfaces of the blocks 228, 234 are also configured with features that set the spacing between them when the dialysis cell is assembled such that the membrane is optimally compressed. Under-compression results in leaks and lateral seepage, while over-compression causes the membrane to be impressed into the channels. Alternatively, the method of assembly may specify that the screws or other fastenings are tightened using a tool with a prescribed torque setting.

The blocks 228, 234 may be fabricated from stainless steel, polyether ether ketone (PEEK), polytetrafluoroethylene (PTFE), polyimide, polycarbonate, glass, ceramic, silicon, plastic, or other suitable material. Holes, trenches, and other features of the dialysis cell may be provided by application of conventional drilling and milling techniques, laser machining, stereophotolithography, wet chemical etching, dry plasma or reactive ion etching, electrochemical or photo-assisted electrochemical etching, ion beam milling, electrical discharge machining, evaporation, thick film deposition, sputtering, electroplating, electroforming, molding, chemical vapor deposition, epitaxy, embossing, and/or contact printing.

The first branch of the second fluidic stream 212 is directed through the first channel 230, while the second branch of the second fluidic stream 214 is directed through the second channel 236. Unwanted low molecular weight components such as sodium chloride, potassium chloride, tris(hydroxymethyl) aminomethane, sodium phosphate, potassium phosphate, glycine, sodium acetate, sodium citrate, urea, ethylenediaminetetraacetic acid, and detergents diffuse from the first channel to the second channel where they are flushed away. The two streams 212, 214 preferably flow in opposite directions through the dialysis cell in order to achieve the maximum possible concentration gradient. High molecular weight biomolecules are unable to pass through the pores of the semi-permeable membrane 232 and are retained in the first branch of the second fluidic stream 212 as it continues to the electrospray emitter 238.

Semi-permeable membranes can be purchased with a specified molecular weight cut-off (MWCO), which is the maximum weight of molecules that can effectively pass through the membrane. Desirably, the specified molecular weight cut-off is selected from the group comprising: (i) 3-10 kDa, (ii) 10-20 kDa, (iii) 20-40 kDa, (iv) 40-60 kDa, (v) 60-80 kDa, and (vi) 80-100 kDa. Suitable membrane materials include, but are not limited to, cellulose ester, regenerated cellulose, and polyvinylidene fluoride. An exemplary material is the standard grade regenerated cellulose dialysis membrane from Spectrum Laboratories, Inc., which has appropriate specifications. It has a working pH range of 2-12, and is compatible with acetonitrile, methanol, ethanol, acetic acid, and formic acid.

To avoid excessive distortion of the membrane 232, the hydrostatic pressures in the first and second channels of the dialysis cell are desirably approximately equal. This can be achieved by adjusting the resistance presented by tubing 239 through appropriate choices of length and internal diameter.

In an alternative embodiment of a system provided in accordance with the present teaching, the semi-permeable membrane is provided as a coating over the inner surface of one of the blocks, rather than as a separate, discrete component. To avoid ingress of the coating material during the coating process, the channels in the block can be temporarily filled with a filler that is later removed with a solvent or by exposure to light. The same result can be achieved more conveniently by immersion of the block in a suitable resin precursor followed by application of stereophotolithography.

Among other benefits, an advantage of systems provided in accordance with the present teaching is that the first and second fluidic streams are essentially independent. The flow rate through the chromatography column can be changed (in order to optimize the conditions for a particular separation) without necessitating a change in the flow rate of the second fluidic stream. In this way, the flow rate of the second fluidic stream is independent of the flow rate through the chromatography column. Consequently, the overall flow rate of the second fluidic stream and the individual flow rates of the first and second branches of the second fluidic stream can be set to provide the optimum speed of response and the optimum dialysis efficiency. It is to be understood that the dialysis cell efficiency is dependent on the rate at which the liquid to be dialyzed flows through the first channel, as the dialysis process requires that the undesired components diffuse to the membrane. When the flow rate is increased, the liquid spends less time in the channel and the fraction of the undesired components that reach the membrane decreases. Hence, operation of a dialysis cell in combination with a periodic sampling module is an advantageous feature of a system provided in accordance with the present teaching, since this configuration allows the dialysis cell to operate at a constant, optimized efficiency, regardless of the flow rate of the first fluidic stream. If required, the operating frequency of the sampling mechanism can be increased or decreased in response to differing chromatographic peak widths or biomolecule concentrations. While the first and second branches of the second fluidic stream could alternatively be provided by two separate pumps and reservoirs, the present teaching makes efficient use of a single pump and reservoir. The system is therefore simpler, more compact, and less expensive.

Desirably, the dialysis cell is gently heated during operation to enhance the rate of diffusion and increase the efficiency with which low molecular weight components are removed. This can be achieved by attaching or integrating heating pads, heating wire, heating tape, electric elements, or thermoelectric elements; by heating the dialysate before it enters the cell; or by circulation of a heated fluid through pipes or channels. The temperature should be chosen to maximize the efficiency but at the same time avoid excessive degradation of the biomolecules and boiling of the solvent. Ideally, a thermocouple should be attached to the dialysis cell in order to allow closed-loop control of the heater power supply. Some very fragile, thermally labile biomolecules are processed in cool rooms to minimize degradation. The efficiency of the dialysis cell may become unacceptably poor in such environments unless it is actively warmed above the ambient temperature. In some applications, dialysis cell heating that is ramped or programmed according to the retention time may be advantageous.

It is known that the rate of dialysis of ionic species can be increased by applying an electric potential difference across the membrane. In FIG. 2, an electric potential difference may be developed by connecting electrodes in contact with the first and second branches of the second fluidic stream (not shown) to a direct current voltage supply.

A power supply 246 provides a high voltage to the emitter 238 for the purpose of inducing electrospray ionization. In some configurations, a portion of the drain current registered by the power supply 246 may be attributed to the flow of current through the fluidic stream to earth via the semi-permeable membrane. This can be prevented by applying an equal high voltage to the three-way connector 210. The drain current registered by the power supply 246 is then a measure of the spray current. The inlet orifice 244 of the mass spectrometer 240 allows a portion of the plume of ions 248 expelled from the electrospray emitter to pass into the vacuum system 242. It is inevitable that both the electrospray emitter 238 and the vacuum interface 242 will eventually become contaminated with residual involatile components in the fluidic stream. In one aspect of the present teaching it is possible to provide interchangeable, modular components such as those described in co-assigned U.S. Pat. No. 7,615,744 B1 and U.S. Pat. No. 8,148,681 B2.

It will be appreciated by someone of skill in the art that various types of mass spectrometer may be used. These include, but are not restricted to cylindrical, toroidal, Paul, and rectilinear ion traps, filters using crossed electric and magnetic fields, magnetic sector analyzers, quadrupole filters, and time-of-flight analyzers. Desirably, a system provided in accordance with the present teaching is of a size and weight consistent with flexible and convenient deployment in a laboratory. Such an implementation may be advantageously constructed using the miniature mass spectrometer described in co-assigned U.S. patent application Ser. No. 13/312,470 and Rapid Communications in Mass Spectrometry, vol. 25, 3281-3288 (2011). Numerous other miniature or compact mass spectrometers have been described, including those that employ discontinuous vacuum interfaces.

To establish a correspondence between the recorded mass spectra and the material collected in each of the vials 108, the time delay associated with the transit of samples from the sampling mechanism 215 to the electrospray emitter 238 can be determined. The delay can be calculated using the known volume of the fluidic pathway and associated flow rates, or established from a test separation. The contents of each vial can then be electronically associated or tagged with a mass spectrum or sequence of mass spectra. For the convenience of the user, the mass spectra are desirably automatically analyzed using software hosted by a system computer to determine the molecular weight of the component in each vial.

Figure 3:
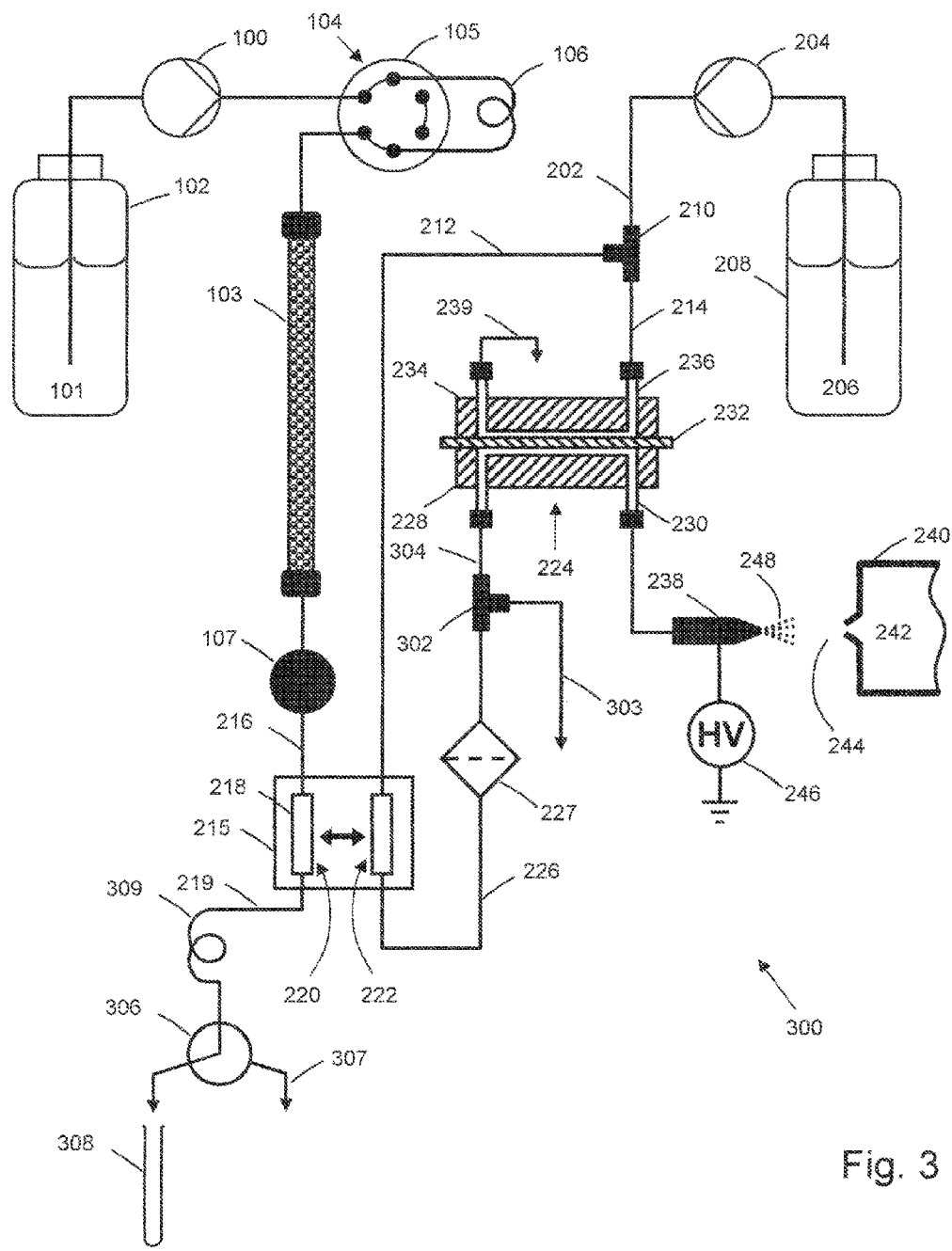
FIG. 3 shows a schematic representation of a second and preferred exemplary system provided in accordance with the present teaching.

FIG. 3 shows a second and preferred implementation of a system provided in accordance with the present teaching in which a portion of the first branch of the second fluidic stream is further diverted or split from the fluidic stream prior to entry into the dialysis cell. This diversion is achieved in this exemplary arrangement by providing a three-way connector 302 downstream of the sampling mechanism 215, which may be considered a flow splitting module of the system. Some of the fluidic stream continues to the first channel of the dialysis cell 230, while the remainder is passed to waste through tubing 303. The ratio of the two flow rates may be referred to as the split ratio. If heat is applied to the dialysis cell in this embodiment, a change in the split ratio is expected, as the viscosity of the fluid in the first channel of the dialysis cell 230 will be less than that of the fluid in the waste leg of the split 303.

The samples transferred from the first fluidic stream are conveyed quickly as far as the three-way connector 302 if the flow rate through tubing 226 is relatively high. By allowing only a portion of the flow to then proceed to the dialysis cell, the amount of fluid that must be treated by the dialysis cell is less than in the implementation of FIG. 2. Consequently, the same dialysis efficiency can be achieved by a smaller dialysis cell that consumes less dialysate. The system may also be configured with the three-way connector 302 positioned downstream of the dialysis cell. However, the advantages relating to dialysis cell size and dialysate consumption are then lost.

A further benefit of this exemplary instance is that the split ratio may be configured such that the flow rate through the dialysis cell is consistent with electrospray emitters designed to operate in the nanoliter to low microliter per minute range. These emitters offer high sensitivity, exhibit a lower susceptibility to ion suppression, and reduce the exposure of the vacuum interface to involatile contaminants. The use of such emitters in any arrangement in which the flow is not split by a flow splitting module as in FIG. 3 would lead to intolerable delays, as all of the dead volume associated with the sampling mechanism, and the tubing between the sampling mechanism and the dialysis cell, would need to be flushed at a rate of nanoliters to low microliters per minute. Given that it may not be practical or convenient to site the bulky sampling mechanism close to the vacuum interface of the mass spectrometer, the dead volume associated with tubing alone may be of the order of 10 μL.

In one advantageous instance, the pump 204 is set to provide the second fluidic stream at a rate of 0.4 mL/min, the waste tube 239 is configured such that the flow rates of the first and second branches of the second fluidic stream 212, 214 are each 0.2 mL/min, and the waste tube 303 is configured such that the flow rate supplied to the emitter 238 is in the range of 0.2 to 5 μL/min.

In an alternative method of operation, the flow rates through the first and/or second channels of the dialysis cell are increased or decreased dynamically in response to changes in the composition of the first fluidic stream resulting from the use of gradient elution methods. For example, in known chromatography methods, the NaCl concentration is ramped from 0.15 M to 0.5 M during the course of a separation. A decrease in the flow rate through the first channel 230 and/or an increase in the flow rate through the second channel 236 may be employed to keep the concentration of NaCl in the solution passed to the electrospray emitter 238 approximately constant during the ramp. Changes to the flow rates through the dialysis cell are effected by motor or solenoid driven valves, or other devices capable of variable fluidic resistance (not shown), connected in series with the waste tubes 239, 303. The valves may be set by the system computer according to the elapsed time since the start of the pre-programmed chromatography method. Alternatively, a software algorithm or dedicated closed-loop electronic circuit may be used to set the valves according to a signal derived from a conductivity meter that monitors either the first fluidic stream, or the first branch of the second fluidic stream at a position downstream of the sampling mechanism. Other advantageous configurations additionally include closed-loop control or programmed ramping of the sampling rate, the flow rate of the second pump 204, and/or the temperature of the dialysis cell.

While all of the separated components can be collected using a fraction collector as in FIG. 2, in some applications it is advantageous to collect only a single desired component. This can be achieved through the use of a diverter valve 306 that switches the flow between a waste outlet 307 and a collection vial 308. A signal derived from the mass spectrometer indicating the presence of a desired component in the first fluidic stream is provided to a logic module of the system, which is configured to vary the position of the diverter valve. When a desired component is detected, the logic module sets the diverter valve such that the flow is directed into the collection vial. At other times the flow is directed to waste. As there is a time delay between sampling and detection, a loop 309 is provided to delay the first fluidic stream until the diverter valve can be set appropriately.

Figure 4:
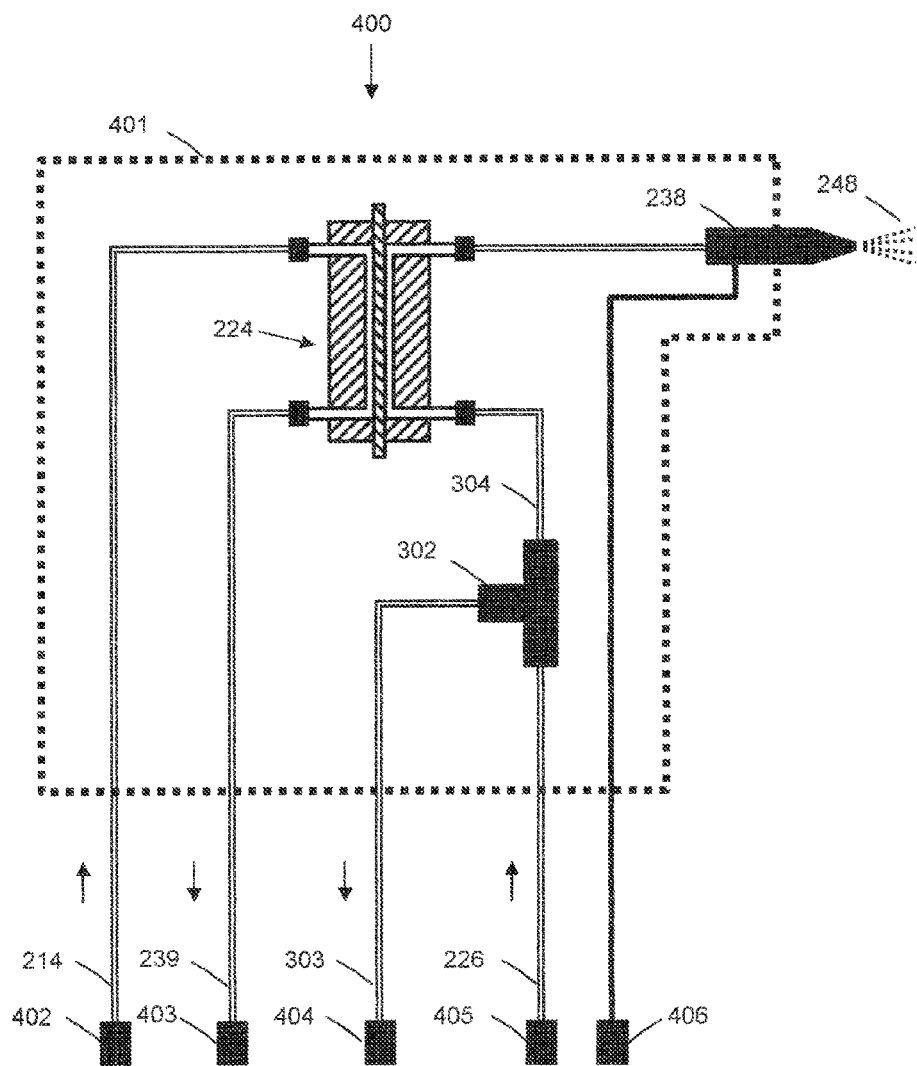
FIG. 4 shows a demountable assembly comprising an electrospray emitter, an in-line dialysis cell, and a static flow splitter.

In order to ensure prompt detection and minimize broadening of chromatographic features due to mixing, the volume of the coupling 304 should be as small as practicable. Accordingly, it is desirable that the three-way connector 302, the dialysis cell 224, and the electrospray emitter 238 are intimately positioned. FIG. 4 shows a demountable assembly 400 into which these three components are integrated. Suitable brackets, fastenings, and locating features secure the components to or within a support structure 401, which may be provided as a base plate or plastic molding. Alternative embodiments may additionally include fittings to supply a flow of gas in a direction coaxial with the emitter. The shear forces exerted on the droplets by the flow of gas assist the nebulization process. As the electrospray emitter 238 needs to be exchanged when it becomes contaminated, the assembly 400 is advantageously configured to allow facile de-coupling of the emitter without disruption of the other components. The demountable assembly 400 is operably positioned within the systems 200 and 300 such that the plume of ions 248 is sampled by the vacuum interface of the mass spectrometer 244. However, the demountable assembly may be entirely removed by releasing fastenings that secure it to the mass spectrometer or another feature of the systems, and disconnecting the fluidic, electrical, and pneumatic couplings 402-406, where provided. Different configurations of the demountable assembly can be easily interchanged in this way.

Figure 5:
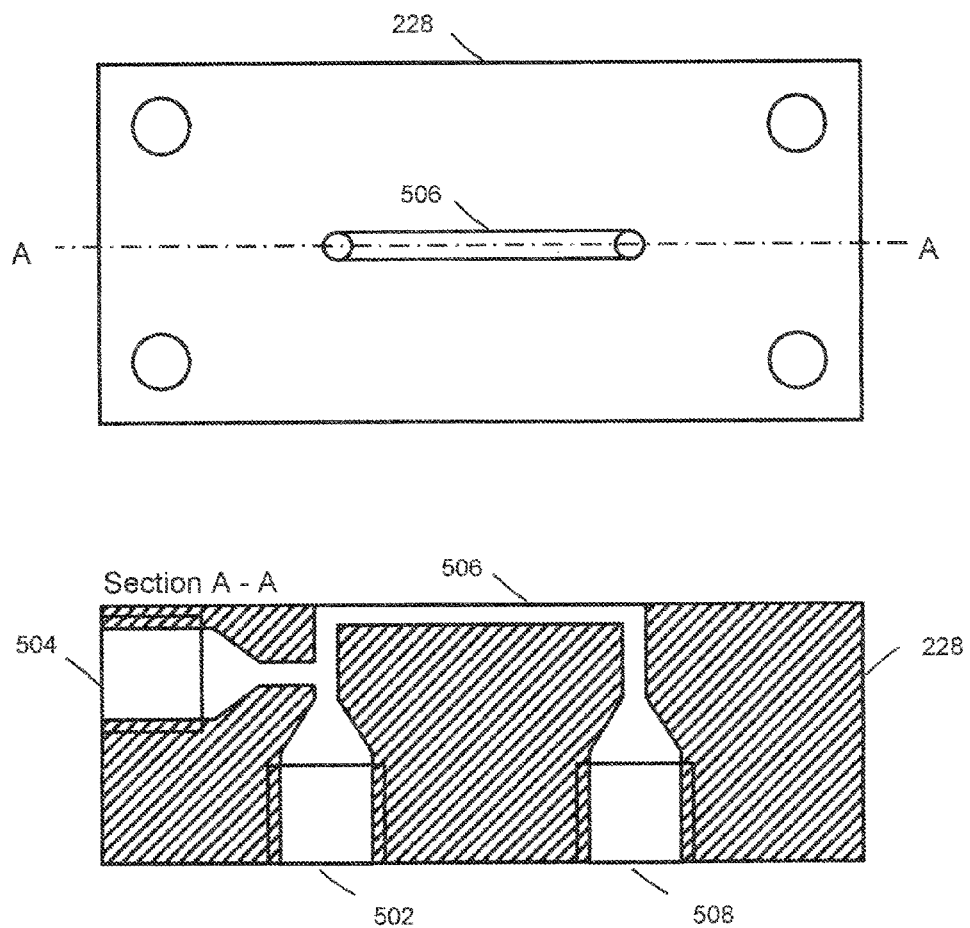
FIG. 5 shows a monolithic structure incorporating both a fluidic split and the first channel of the dialysis cell.

Although the dead volume associated with coupling 304 in FIG. 3 can be minimized by using narrow internal diameter tubing, for example 25 μm internal diameter PEEK capillary tubing, a further reduction may be realized if the fluidic split 302 and the first channel of the dialysis cell 230 are co-fabricated as a monolithic component. An exemplary instance is shown in FIG. 5. The fluidic stream enters through channel 502 and is then split. Most of the fluidic stream leaves through channel 504 while the rest passes directly through a channel 506 that is in contact with the semi-permeable membrane when the dialysis cell 224 is assembled. Each of the fluidic ports is advantageously fabricated with thread and conical sections that engage with standard nut and ferrule tube fittings.

Figure 6:
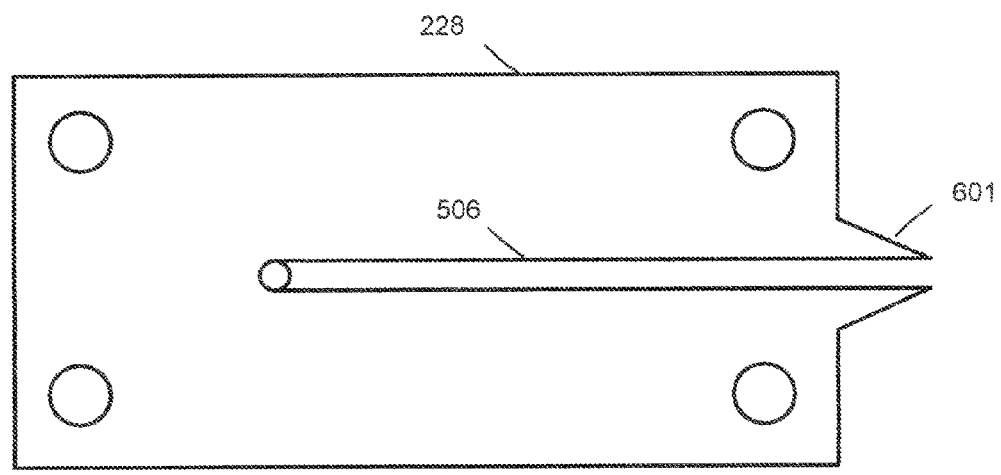
FIG. 6 shows a monolithic structure incorporating both the first channel of the dialysis cell and the electrospray emitter.

The dead volume may be reduced still further by eliminating the fittings needed to couple the dialysis cell to a separate electrospray emitter. FIG. 6 shows a monolithic structure in which the electrospray emitter 601 and the first channel of the dialysis cell 506 are also co-fabricated. Desirably, this is provided as a disposable and consumable component.

Figure 7:
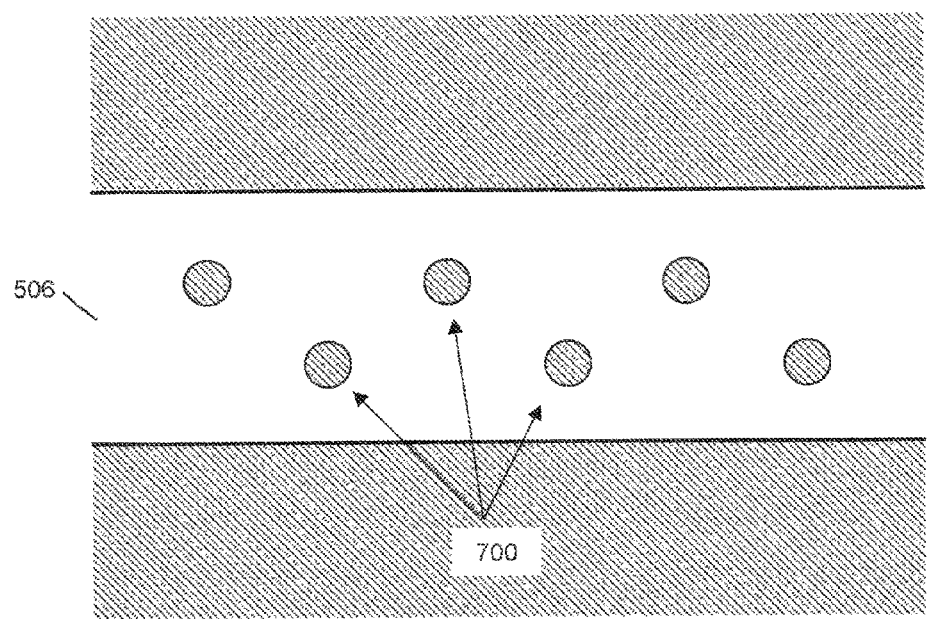
FIG. 7 shows a section of the first channel configured with a series of membrane support pillars.

The open channel 506 in FIGS. 5 and 6 also contributes to the volume that must be swept by the fluidic stream. By reducing the depth of the channel as far as is practicable, the associated delay can be minimized without changing the area of the membrane in contact with the fluidic stream. However, it is likely that very shallow channels will become constricted when small pressure differences cause the deformable membrane to ingress. FIG. 7 shows a plan view of a section of the open channel 506 that has been configured with a series of support pillars 700. As the unsupported span is reduced, shallower channel depths may be employed. Advantageously, the channel and the pillars therein are fabricated by first transferring the pattern from a mask to a resist layer using photolithography, and then selectively removing material by application of an etching technique. The membrane may also be supported by providing one or more axial ribs or transverse beams within the channel. The optimum channel volume depends on the duration of the chromatographic separation and the dead volumes of the various fluidic couplings. However, for electrospray flow rates of 0.2 to 5 µL/min, a channel volume in the range of 0.10 to 2.5 µL is of general applicability.

Figure 8:
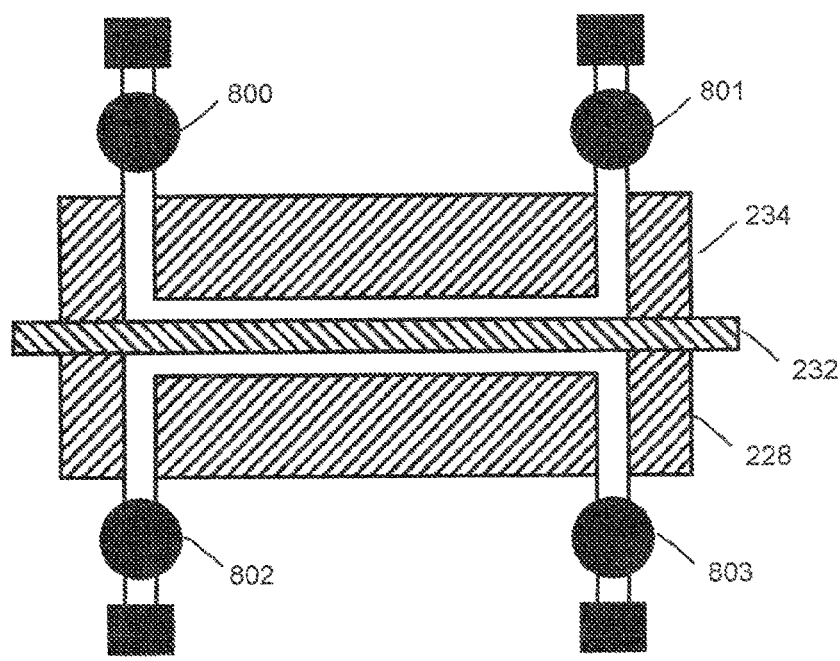
FIG. 8 shows how in-line conductivity meters may be positioned to give a continuous measurement of the efficiency of the dialysis cell.

FIG. 8 shows a modification that allows the efficiency of the dialysis process to be monitored continuously during operation. In-line conductivity meters 800-803 provide a measure of the extent to which low molecular weight ionic components are removed from the first branch of the second fluidic stream. This information may be used to monitor any long-term degradation of the dialysis efficiency and indicate when the membrane should be exchanged. Alternatively, conductivity measurements may be used to make dynamic adjustments to the system in response to a change in the composition of the first fluidic stream, as described in connection with FIG. 3. For example, the conductivity measured by meter 802 may be used to automatically direct changes in the dialysate flow rate.

While four conductivity meters are shown in FIG. 8, it is to be understood that other embodiments with fewer conductivity meters are also in accordance with the present teaching. Furthermore, electrochemical detectors, pH meters, or UV adsorption cells may be advantageously employed in place of, or in series with one or more of the conductivity meters. To minimize dead volume delays and eliminate the inconvenience of additional fluidic connections, the meters 800-803 are desirably co-fabricated with the dialysis cell using microengineering techniques, which include laser machining, wet chemical etching, dry plasma or reactive ion etching, electrochemical or photo-assisted electrochemical etching, ion beam milling, electrical discharge machining, evaporation, thick film deposition, sputtering, electroplating, electroforming, molding, chemical vapor deposition, epitaxy, embossing, and/or contact printing.

Figure 9:
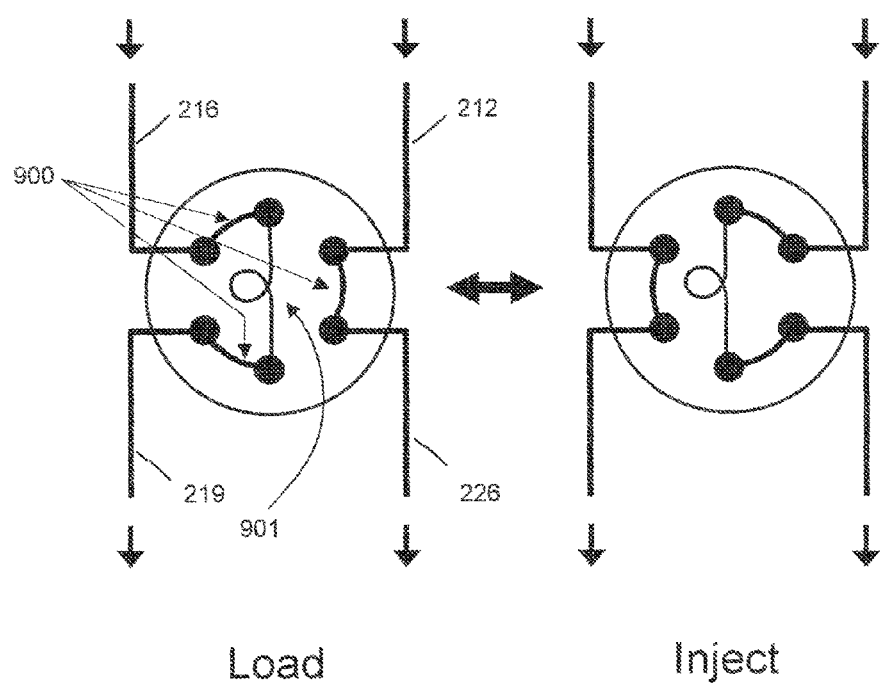
FIG. 9 illustrates the operation of a loop injection valve that may be used to the same effect as a mass rate attenuator.

It will be understood by a person of skill in the art that the function of the mass rate attenuator 215 in FIGS. 2 and 3 could equally be achieved using a motor or solenoid driven loop injection valve. The load and inject sequence is illustrated in FIG. 9. During the load step, the channels in the valve rotor 900 are oriented such that the first fluidic stream passes through a loop 901 connected to two opposing ports. Periodically, the valve rotor turns through 60°, thereby injecting the contents of the loop into the first branch of the second fluidic stream.

Figure 10:
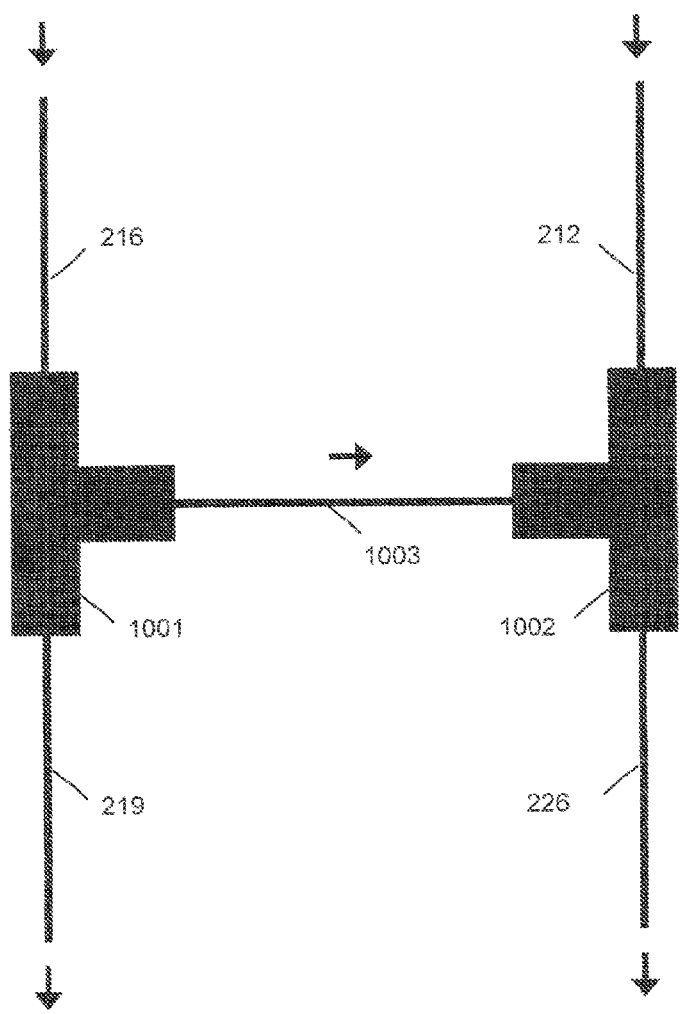
FIG. 10 shows a static fluidic split arrangement that may be used instead of a periodic sampling mechanism.

FIG. 10 shows how a static split comprising two three-way connectors 1001, 1002 may be used instead of a periodic sampling mechanism. The fluidic resistance presented by tubing 219 is adjusted such that a small, fixed fraction of the first fluidic stream continuously passes through transfer tubing 1003 and joins the second fluidic stream 212 at three-way connector 1002. The delay associated with the transit of fluid through tubing 1003 at a low flow rate can be minimized by intimately positioning the three-way connectors, or by co-fabricating the three-way connectors and the transfer tube as a monolithic structure.

Figure 11:
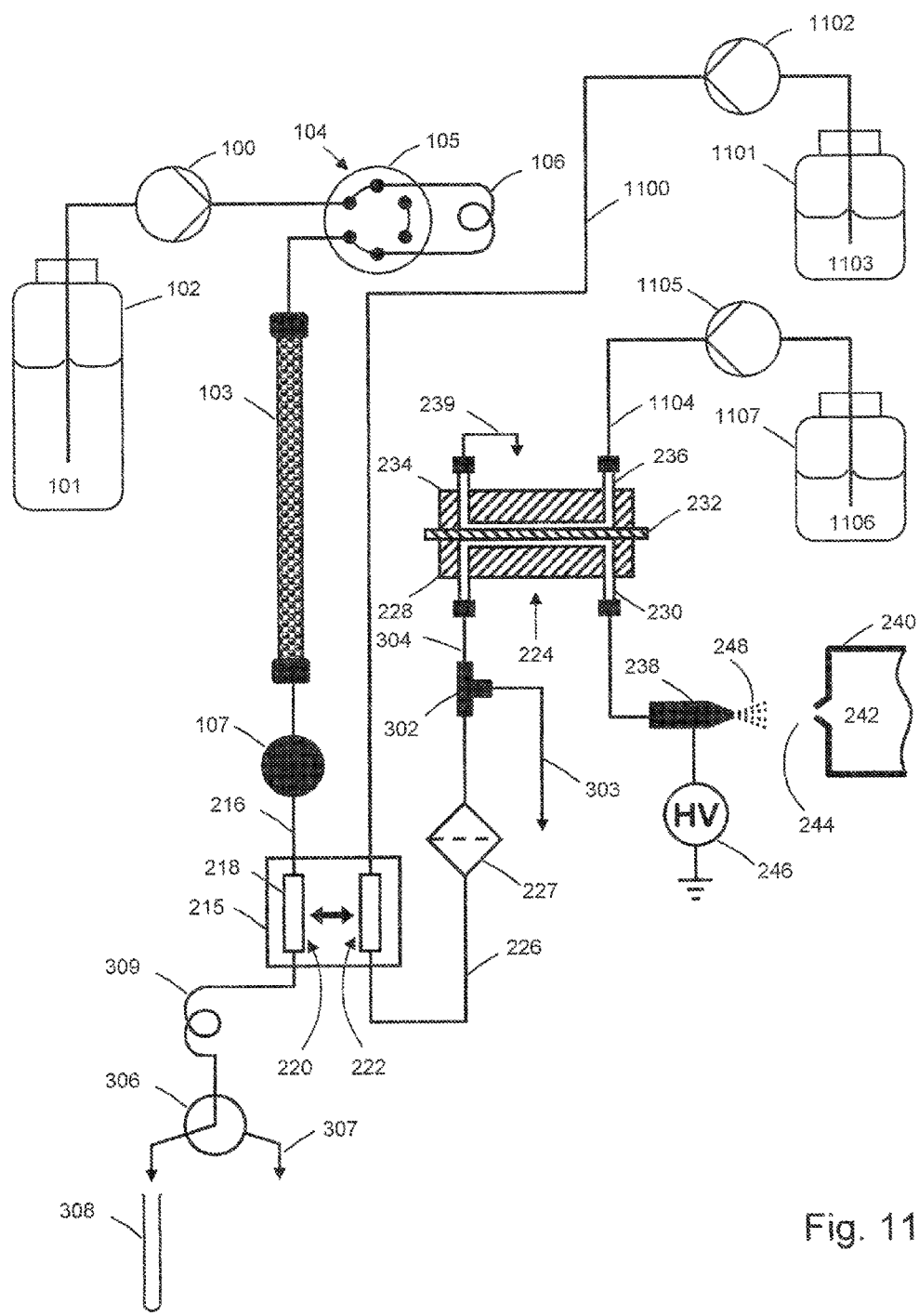
FIG. 11 shows a schematic representation of a third embodiment of a system provided in accordance with the present teaching in which a third fluidic stream is provided.

A minor disadvantage of the arrangements shown in FIGS. 2 and 3 is that the sampling chamber 218 transfers a small amount of the solvent system 206 into the first fluidic stream 216 when it returns to flow path 220 after being flushed. The amount of organic solvent introduced into the first fluidic stream via this route is unlikely to exceed 0.5%. In the event that this compromises the integrity of the biomolecules being separated, the modification shown in FIG. 11 is preferred. Here, the samples are flushed from the sampling mechanism 215 and conveyed to the dialysis cell 224 by a second fluidic stream 1100 that is drawn from a reservoir 1101 by pump 1102. The solvent system 1103 does not contain organic solvents or chemical modifiers and desirably comprises of water only. The samples taken from the first fluidic stream are conveyed quickly as far as the three-way connector 302, where the flow is split such that a minor fraction continues through the first channel of the dialysis cell and thereafter to the electrospray emitter. Hence, the time delay due to transit of the samples through the system and the amount of fluid that must be treated by the dialysis cell are simultaneously minimized, in accordance with the present teachings. Dialysate is provided as a separate fluidic stream 1104 by a third pump 1105, which draws a solvent system 1106 from a reservoir 1107. An organic solvent and chemical modifier may be injected into the second fluidic stream at any position downstream of the sampling mechanism 215. This can be conveniently achieved by adding the organic solvent and chemical modifier to the solvent system 1106 with the intention that both will subsequently diffuse across the semi-permeable membrane 232.

Figure 12:
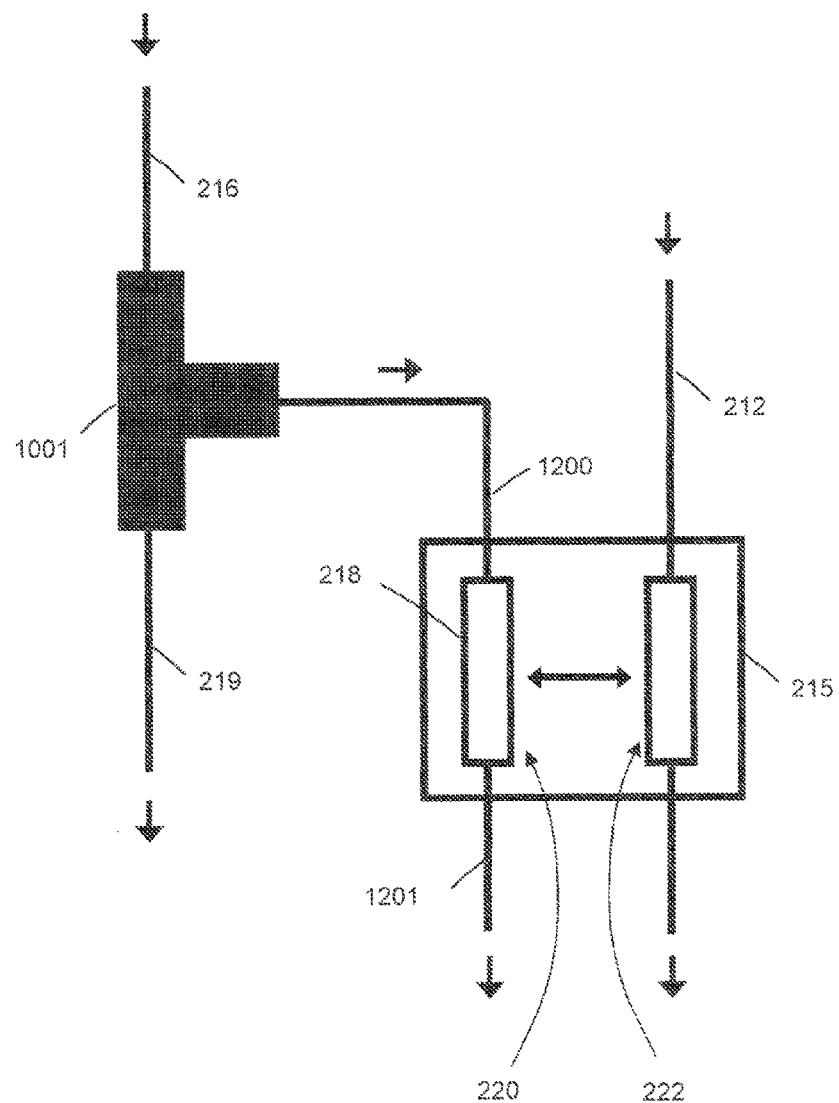
FIG. 12 shows a static fluidic split arrangement coupled to a periodic sampling mechanism.

An alternative modification that avoids the need for a third pump is shown in FIG. 12. The three-way connector 1001 allows a minor fraction of the first fluidic stream to be diverted through tubing 1200 and into the left-hand side flow channel 220 of the periodic sampling mechanism 215, where it is periodically transferred into the second fluidic stream, 212. Any excess fluid, including the small amount of solvent system 206 transferred from the second fluidic stream on return of the chamber 218 to flow path 220, passes to waste through tubing 1201. However, the dead volume of tubing 1200 should be very low in order that analysis of the first fluidic stream is not significantly delayed by the slow passage of fluid through this component. Advantageously, the three-way connector 1001 and the tubing 1200 are integrated into the stator of the sampling mechanism, 215, such that the dead volume is negligibly small.

While exemplary arrangements have been described herein to assist in an understanding of the present teaching it will be understood that modifications can be made without departing from the spirit and or scope of the present teaching. To that end it will be understood that the present teaching should be construed as limited only insofar as is deemed necessary in the light of the claims that follow. Furthermore, the words comprises/comprising when used in this specification are to specify the presence of stated features, integers, steps or components but does not preclude the presence or addition of one or more other features, integers, steps, components or groups thereof.

The invention claimed is:

1. A system for effecting biomolecule separations and monitoring said separations by mass spectrometry, the system comprising:
   a liquid chromatography module configured to effect at least a partial separation of biomolecule components dissolved in a liquid, the dissolved biomolecule components being carried through the liquid chromatography module in a first fluidic stream;
   a sampling module in fluid communication with and provided downstream of the liquid chromatography module, the sampling module being configured to periodically transfer an aliquot of the liquid in the first fluidic stream into a second fluidic stream;
   a dialysis module in fluid communication with and provided downstream of the sampling module, the dialysis module being configured to dialyse the liquid in the second fluidic stream;
   a mass spectrometer in fluid communication with and provided downstream of the dialysis module, the mass spectrometer being configured to detect components in the dialysed liquid in the second fluidic stream; and,
   a flow splitting module configured to split the second fluidic stream, the flow splitting module being provided downstream of the sampling module and prior to the dialysis module, the splitting of the second fluidic stream effecting a reduction in the flow of liquid that is passed into and dialysed by the dialysis module;
   wherein operably, the first fluidic stream is provided at a first flow rate and the second fluidic stream is provided at a second flow rate, independent of the first flow rate such that the dialysis module operates at a constant flow rate.

2. The system of claim 1 wherein the dialysis module comprises a first channel and a second channel, the first channel being configured to receive the liquid to be dialysed and the second channel being configured to receive a dialysate.

3. The system of claim 2 wherein the second fluidic stream comprises a first branch and a second branch, the first branch of the second fluidic stream operably receiving the transferred aliquot and thereafter passing through the first channel, the second branch of the second fluidic stream being operably directed through the second channel.

4. The system of claim 1 wherein the sampling module comprises a mass rate attenuator.

5. The system of claim 1 wherein the sampling module comprises a loop injection valve.

6. The system of claim 2 wherein the first and second channels of the dialysis module are separated by a semipermeable membrane.

7. The system of claim 2 wherein the flow splitting module is integrally formed with the first channel of the dialysis module.

8. The system of claim 2 wherein the flow rate through the first channel of the dialysis module is operably in the range of 0.2 to 5 microliters per minute.

9. The system of claim 1 wherein the biomolecule components comprise at least one of: proteins, peptides, polypeptides, antibodies, enzymes, hormones, oligosaccharides, lipids, nucleic acids, and oligonucleotides.

10. The system of claim 1 wherein the second fluidic stream comprises one or more organic solvents selected from acetonitrile, methanol, isopropanol, and ethanol.

11. The system of claim 1 wherein the second fluidic stream comprises one or more chemical modifiers that aid in an ionisation process within the mass spectrometer.

12. The system of claim 1 wherein the mass spectrometer is configured to provide ionisation achieved by means of electrospray ionisation, atmospheric pressure chemical ionisation, atmospheric pressure photoionisation.

13. The system of claim 1 comprising a diverter valve to operably divert the first fluidic stream into a collection vessel.

14. The system of claim 13 further comprising a logic module configured to vary the position of the diverter valve based on information derived from the mass spectrometer.

15. The system of claim 1 comprising a system computer configured to store data from the mass spectrometer in the form of stored mass spectra, the system computer further configured to derive the molecular weights of detected components from the stored mass spectra.

16. The system of claim 2 comprising at least one meter to monitor at least one of the fluidic streams passing through the first and second channels such that the efficiency of the dialysis process is indicated.

17. The system of claim 16 comprising a pump configured to vary flow rates in the first or second channels according to the indicated efficiency.

18. The system of claim 1 comprising a first liquid chromatography module and a second liquid chromatography module, the system further comprising a multiplexer provided between each of the first liquid chromatography module and the mass spectrometer and the second liquid chromatography module and the mass spectrometer, the multiplexer configured to provide samples from either the first liquid chromatography module or the second liquid chromatography module to the mass spectrometer.

19. The system of claim 1 comprising an electrospray emitter.

20. The system of claim 19 provided in a modular construct, wherein at least the electrospray emitter and the dialysis module are provided as a demountable assembly.

21. The system of claim 20, provided in a modular construct, wherein at least the electrospray emitter and the dialysis module are provided as a demountable assembly and wherein the first channel of the dialysis module and the electrospray emitter are provided as a monolithic structure.

22. The system of claim 6 wherein the molecular weight cut-off of the semipermeable membrane is selected from the group consisting of: (i) 3-10 kDa, (ii) 10-20 kDa, (iii) 20-40 kDa, (iv) 40-60 kDa, (v) 60-80 kDa, and (vi) 80-100 kDa.

23. A method of effecting biomolecule separations and monitoring said separations by mass spectrometry, the method comprising:
   using a liquid chromatography module to effect at least a partial separation of biomolecule components dissolved in a liquid, the dissolved biomolecule components being carried through the liquid chromatography module in a first fluidic stream;

using a sampling module in fluid communication with and provided downstream of the liquid chromatography module, the sampling module being configured to periodically transfer an aliquot of the liquid in the first fluidic stream into a second fluidic stream;

providing a dialysis module in fluid communication with and provided downstream of the sampling module, the dialysis module being configured to dialyse the liquid in the second fluidic stream; and providing a mass spectrometer in fluid communication with and provided downstream of the dialysis module, the mass spectrometer being configured to detect components in the dialysed liquid in the second fluidic stream;

wherein operably, the first fluidic stream is provided at a first flow rate and the second fluidic stream is provided at a second flow rate, independent of the first flow rate such that the dialysis module operates at a constant flow rate.

24. The method of claim 23 comprising electronically tagging or labelling collected portions of the first fluidic stream with mass spectra or molecular weights of biomolecules contained therein.

25. A system for effecting biomolecule separations and monitoring said separations by mass spectrometry, the system comprising:

a liquid chromatography module configured to effect at least a partial separation of biomolecule components dissolved in a liquid, the dissolved biomolecule components being carried through the liquid chromatography module in a first fluidic stream;

a sampling module in fluid communication with and provided downstream of the liquid chromatography module, the sampling module being configured to periodically transfer an aliquot of the liquid in the first fluidic stream into a second fluidic stream;

a dialysis module in fluid communication with and provided downstream of the sampling module, the dialysis module being configured to dialyse the liquid in the second fluidic stream; and a mass spectrometer in fluid communication with and provided downstream of the dialysis module, the mass spectrometer being configured to detect components in the dialysed liquid in the second fluidic stream;

wherein operably, the first fluidic stream is provided at a first flow rate and the second fluidic stream is provided at a second flow rate, independent of the first flow rate such that the dialysis module operates at a constant flow rate; and wherein the dialysis module comprises a first channel and a second channel, the first channel being configured to receive the liquid to be dialysed and the second channel being configured to receive a dialysate and wherein the second fluidic stream comprises a first branch and a second branch, the first branch of the second fluidic stream operably receiving the transferred aliquot and thereafter passing through the first channel, the second branch of the second fluidic stream being operably directed through the second channel.

* * * * *